United States Patent [19]
Puente

[11] Patent Number: 5,248,591
[45] Date of Patent: Sep. 28, 1993

[54] DIAGNOSIS OF CANCER AND OTHER PROLIFERATIVE DISORDERS BY ANALYSIS OF PROTHYMOSIN ALPHA EXPRESSION

[76] Inventor: Fernando D. Puente, Guldris s/n, Cacheiras-Teo (La Coruna), Spain

[21] Appl. No.: 694,800

[22] Filed: May 2, 1991

[51] Int. Cl.5 .................. C12Q 1/00; G01N 33/53
[52] U.S. Cl. ................................ 435/7.1; 436/542
[58] Field of Search .............. 435/6, 7.1; 436/542

[56] References Cited
PUBLICATIONS

Walker et al. (1989), Br. J. Cancer 60, 426–429.
Oates et al. (1990), J. Cell. Biochem. (Suppl.), vol. 14 Part E, p. 94.
Hedley et al. (1987), Cancer Res. 47, 4729–4735.

*Primary Examiner*—Richard A. Schwartz
*Assistant Examiner*—Philip W. Carter
*Attorney, Agent, or Firm*—Ostrolenk, Faber, Gerb & Soffen

[57] ABSTRACT

The diagnosis of patients with cancer and other proliferative disorders may be effectively established by the estimation of the expression of prothymosin alpha.

4 Claims, No Drawings

DIAGNOSIS OF CANCER AND OTHER PROLIFERATIVE DISORDERS BY ANALYSIS OF PROTHYMOSIN ALPHA EXPRESSION

FIELD OF THE INVENTION

The present invention relates to the diagnosis of cancer and other proliferative disorders by means of the analysis of prothymosin alpha expression.

BACKGROUND OF THE INVENTION

Despite well-documented successes in earlier detection of breast cancer, age-adjusted death rates have improved marginally in recent years. One postulated reason for this failure to effect more dramatic improvement in outcome is that tumor cell dissemination occurs very early, negating much of the survival advantage of early diagnosis. Recognition of early dissemination in many patients has forced clinical oncologists and surgeons to rethink the general philosophy of treatment of breast cancer. Effective application of individualized therapy will eventually require more precise identification of patients at high risk for local recurrence and distant metastasis (Visscher et al., Pathology Annual 25:171-210, 1990).

Cell proliferation is a necessary step for tumor development. Not surprisingly, cell proliferation indices have been shown to be prognosis-related (Munro *Diagn Oncol* 1:53-63, 1991). However, several problems limit today techniques that estimate cell proliferation (Visscher et al. Op. cit.). Prothymosin alpha expression has been shown to be associated with cell division (Rosen et al., *Histochemistry* 94:597-599, 1990) pointing to the fact that prothymosin alpha could play a basic role in normal cell division that is also conserved in tumor cells. Until now, all of the known cell proliferation indices have several problems that limit their effective application in the precise identification of patients at high risk for local recurrence and distant metastasis.

SUMMARY OF THE INVENTION

Prothymosin alpha expression is easily detected in tissues. Therefore, its determination in tumor samples could be used as a cell proliferation marker that overcomes the several problems that limit the wide application of other cell proliferation indices.

It has now been shown that effective application of individualized therapy of tumors greatly depends on a precise identification of patients at high risk for local recurrence and distant metastasis. The analysis of prothymosin alpha expression in tumor samples can be used to estimate the proliferative activity of the tumor and thus evaluate the risk for local recurrence and distant metastasis.

DETAILED DESCRIPTION OF THE INVENTION

An effective cell proliferation marker has now been found. This marker involves the assay of prothymosin alpha levels, which includes prothymosin aplha derivative or fragment peptides, in tumor samples.

The measure of prothymosin alpha levels or the measure of prothymosin alpha derivative peptides such as thymosin alpha 1, an $NH_2$ terminal fragment, or other fragments from or related to prothymosin alpha molecule provides a precise identification of patients at high risk for local recurrence and distant metastasis.

Patients

Tumors were obtained from a series of fifty-two consecutive female patients with classic invasive ductal carcinoma who underwent definitive surgery at the Hospital General de Galicia (Santiago de Compostela, Spain) from 1987 through 1989. No patients received adjuvant chemotherapy or hormonal therapy. Patients with a second malignant neoplasm were rejected.

Prothymosin Alpha Radioimmunoassay

Small slices of tumor and normal tissues obtained during surgery were homogenized with a Polytron homogenizer in PBS-EDTA (phosphate buffered saline 0.05 M, pH 7.5; EDTA, 2 mM) centrifuged at 14,000×g for 15 minutes and the supernatant analyzed for prothymosin alpha and total protein. The radiolabeled ligand was $I^{125}$-Tyr*-thymosin $\alpha_1$. Synthetic thymosin $\alpha_1$ was employed to standardize the assay. The antibody employed in the experiments reported here was raised against synthetic thymosin $\alpha_1$ (Roson et al. *Histochemistry* 94:597-599, 1990). The mean intra-assay coefficient of variation was 10%. To avoid interassay variations, normal and tumor samples from a subject were run in the same assay. In order to convert tissue prothymosin alpha to thymosin $\alpha_1$ we did not take any special precaution during the extraction procedure (Haritos et al. *Proc.Natl Acad.Sci.USA* 81-1008-1011, 1984); therefore, the results are expressed as thymosin $\alpha_1$ equivalents.

Expression of Prothymosin Alpha In Tumor Cells

Prothymosin alpha levels in tumor samples were significantly greater $p < 0.0001$) than prothymosin alpha levels found in adjacent normal breast tissue samples obtained from the same patient.

By means of immunohistochemical techniques, it is corroborated that tumor cells were actually expressing prothymosin alpha.

Prothymosin Alpha Levels and the Clinical Stage of the Patients

Tumors were divided in four stages according to the following criteria. Stage I, the tumor is small, limited to the breast and without metastasis (18 patients); Stage II, there is axillary metastasis (21 patients); Stage III, advanced locoregional disease is present (8 patients); and Stage IV, there is distant metastasis (4 patients). Patients were divided into two groups: (A) those who have prothymosin alpha levels lower than 124 ng of thymosin alpha 1 per mg of protein; and (B) those who have prothymosin alpha levels greater than 124 ng of thymosin alpha 1 per mg of protein. In Table I, cross-tabulation of patients (groups A and B) by clinical stage is shown.

TABLE I

PROTHYMOSIN ALPHA LEVELS IN RELATION TO THE CLINICAL STAGE

| | Clinical Stage | | | |
|---|---|---|---|---|
| | I | II | III | IV |
| A[1] | 12 (67%) | 2 (9.5%) | 4 (50%) | 1 (25%) |
| B[2] | 6 (33%) | 19 (90.5%) | 4 (50%) | 3 (75%) | number of patients (percent)
[1] Prothymosin alpha levels lower than 124 ng of thymosin alpha 1 per mg protein.
[2] Prothymosin alpha levels greater than 124 ng of thymosin alpha 1 per mg protein.

As of January 1991, all the Stage I patients in Group A did not present local recurrence or distant metastasis. Node-negative patients at high risk exhibited prothymosin alpha levels greater than 124 ng (40 picomoles) of thymosin alpha 1 per mg of protein, as will be discussed below.

Prothymosin Alpha Levels and Positive Axillary Lymph Nodes

Forty-nine patients were divided into four groups according to the following criteria: (1) patients without positive nodes (22 patients); (2) patients with less than four positive nodes (10 patients); (3) patients with four to seven positive nodes (9 patients); and (4) patients with more than seven positive nodes (8 patients). Prothymosin alpha levels in breast cancers with nodal metastasis was significantly higher than in those cancers without lymph node involvement ($p<0.0001$). Crosstabulation of patients according to prothymosin alpha levels (Groups A or B, see before) by the number of positive nodes is seen in Table II. An association between both parameters was found ($p=0.007$).

TABLE II

PROTHYMOSIN ALPHA LEVELS IN RELATION TO THE AXILLARY LYMPH-NODE STATUS

| | Number of Positive Nodes | | | |
| --- | --- | --- | --- | --- |
| | 0 | 1-3 | 4-7 | >7 |
| A[1] | 14 | 3 | 2 | 0 |
| | (64%) | (30%) | (22%) | (0%) |
| B[2] | 8 | 7 | 7 | 8 |
| | (36%) | (70%) | (78%) | (100%) | number of patients (percent)
[1] Prothymosin alpha levels lower than 124 ng of thymosin alpha 1 per mg protein.
[2] Prothymosin alpha levels greater than 124 ng of thymosin alpha 1 per mg protein.

Prothymosin Alpha Levels and the Histological Grade

Tumors were divided into cytologic types (A, B, AB and C), according to Dawson's criteria. It is worth noting that 78% of patients with cytologic Type B, the poorest prognostic factor, had prothymosin alpha levels greater than 124 ng of thymosin alpha 1 per mg of protein. On the other hand, 50% of patients graded A and 33% of patients graded C had prothymosin alpha levels greater than 124 ng of thymosin alpha 1 per mg of protein.

TABLE III

PROTHYMOSIN ALPHA LEVELS IN RELATION TO THE HISTOLOGICAL GRADE

| | Histological Grade | | | |
| --- | --- | --- | --- | --- |
| | A | B | AB | C |
| A[1] | 5 | 5 | 3 | 4 |
| | (50%) | (22%) | (30%) | (67%) |
| B[2] | 5 | 18 | 7 | 2 |
| | (50%) | (78%) | (70%) | (33%) | number of patients (percent)
[1] Prothymosin alpha levels lower than 124 ng of thymosin alpha 1 per mg protein.
[2] Prothymosin alpha levels greater than 124 ng of thymosin alpha 1 per mg protein.

Present data is in agreement with previous reports that stressed the importance of proliferating indices in the prognosis of node-negative breast tumors. By means of chi-square analysis, it was found that tumor prothymosin alpha levels and the number of involved axillary lymph nodes were associated parameters. Moreover, it was also found that prothymosin alpha levels are high in 75% of Stage IV patients, suggesting that prothymosin alpha levels could be used as a marker of the metastatic potential of breast tumors. Further support to this claim comes from the finding that 75% histological graded B tumors—those with the highest metastatic potential—had high prothymosin alpha levels. Of special relevance is the fact that all node negative Stage I patients with prothymosin alpha levels lower than 124 ng of thymosin alpha 1 did not present local recurrences or distant metastasis after a two-year follow-up. On the other hand, 50% node negative Stage I patients with prothymosin alpha greater than 124 ng of thymosin alpha 1 per mg protein had local recurrences or distant metastasis after two years.

Prothymosin alpha expression is not a specific feature of metastasis--since prothymosin alpha is also found in normal tissues--but is instead a measure of the proliferating activity of the tumor and thus of its metastatic potential.

In summary, the estimation of tumor prothymosin alpha levels might help to identify Stage I patients at high risk for local recurrence and distant metastasis.

Although the present invention has been described in relation to particular embodiments thereof, many other variations and modifications and other uses will become apparent to those skilled in the art. It is preferred, therefore, that the present invention be limited not by the specific disclosure herein, by only by the appended claims.

What is claimed is:

1. A method of estimating the risk of local recurrence or distant metastasis of breast cancer, comprising obtaining a tumor sample from a patient to be tested and measuring levels of prothymosin alpha and/or thymosin alpha-1 in said tumor sample; wherein a prothymosin alpha or thymosin alpha-1 level equal to or greater than 40 picomoles per milligram of total protein in said tumor sample indicates a high risk of local recurrence or distant metastasis of breast cancer.

2. The method of claim 1, wherein the measuring comprises measuring the level of prothymosin alpha in said tumor sample.

3. The method of claim 1, wherein the measuring comprises measuring the level of thymosin alpha-1 in said tumor sample.

4. The method of claim 1, wherein the measuring comprises measuring the levels of prothymosin alpha and thymosin alpha-1 in said tumor sample.

* * * * *